(12) United States Patent
Lifshitz (10) Patent No.: US 6,689,392 B2
(45) Date of Patent: Feb. 10, 2004

(54) METHODS AND COMPOSITIONS FOR CONTROLLING PLANT PATHOGEN

(75) Inventor: Ran Lifshitz, Ramat Gan (IL)

(73) Assignee: Agricare Ltd., Ramat Gan (IL)

( * ) Notice: Subject to any disclaimer, the term of this patent is extended or adjusted under 35 U.S.C. 154(b) by 55 days.

(21) Appl. No.: 10/058,108

(22) Filed: Jan. 29, 2002

(65) Prior Publication Data

US 2002/0160054 A1 Oct. 31, 2002

Related U.S. Application Data (60) Provisional application No. 60/264,285, filed on Jan. 29, 2001.

(51) Int. Cl.[7] ............... A01N 37/36; A01N 37/44; A01N 55/00; A01N 55/02; A01N 59/00; A01N 59/06; A01N 59/16; A01N 59/20; A01N 59/26

(52) U.S. Cl. ............ 424/638; 514/558; 514/561; 514/564; 514/568; 514/572; 514/574; 514/784; 514/141; 514/142; 514/494; 514/499; 514/500; 514/502; 514/553; 514/557; 504/101; 424/600; 424/601; 424/602; 424/604; 424/605; 424/606; 424/617; 424/630; 424/631; 424/632; 424/633; 424/634; 424/635; 424/637; 424/639; 424/640; 424/641; 424/646; 424/647; 424/648; 424/675; 424/677; 424/678; 424/682; 424/683; 424/684; 424/685; 424/686; 424/687; 424/688; 424/689; 424/690; 424/691; 424/692; 424/693; 424/694; 424/695; 424/696; 424/697; 424/698; 424/DIG. 6

(58) Field of Search ............... 424/641, 605, 424/600–602, 604, 606, 617, 630–635, 637–640, 646–648, 675, 677, 678, 682–698, DIG. 6; 514/494, 557, 574, 141, 142, 499, 500, 502, 553, 558, 561, 564, 568, 572, 784; 504/101

(56) References Cited

U.S. PATENT DOCUMENTS

| | | |
|---|---|---|
| 4,075,324 A | 2/1978 | Thizy et al. |
| 5,674,536 A | 10/1997 | Burkhart et al. |

FOREIGN PATENT DOCUMENTS

| | | | |
|---|---|---|---|
| WO | 99/53760 | * | 10/1999 |
| WO | 00/62609 | * | 10/2000 |

OTHER PUBLICATIONS

Derwent Abstract, accession No. 1994–360359, abstracting IL 97676 (Oct. 1994).*

Chemical Abstracts 122:125949, abstracting IL 97676 (Oct. 1994).*

* cited by examiner

*Primary Examiner*—John Pak
(74) *Attorney, Agent, or Firm*—Eitan, Pearl, Latzer & Cohen Zedek, LLP (57) ABSTRACT

A composition for controlling growth of pathological organisms on a plant, said composition comprises an effective amount of one or more of metal ion(s); one or more of chelating agent(s); and phosphorous acid, and/or salt or hydrate thereof, said composition is in an agriculturally compatible carrier or vehicle.

26 Claims, 4 Drawing Sheets

# METHODS AND COMPOSITIONS FOR CONTROLLING PLANT PATHOGEN

CROSS-REFERENCE TO RELATED APPLICATIONS

The present application claims priority from U.S. provisional application serial No. 60/264,285, filed Jan. 29, 2001.

FIELD OF THE INVENTION

The present invention relates to compositions and methods for controlling plant pathogens by contacting the plant or the soil which surround the plant with a composition comprising an effective amount of at least one metal ion, at least one chelating agent and at least one phosphorous acid, a salt or hydrate thereof.

BACKGROUND OF THE INVENTION

Global regulatory requirements are becoming more and more demanding with respect to the use of pesticides, particularly with respect to unmanaged or unnecessary pesticide residues. Thus, there exist mutually contradictory requirements of farmers in that the need to control destructive pathogens demands that more pesticide be used, while increasing pressures from regulatory agencies demand that less pesticide be used. These regulatory demands are aimed to protect the safety and health of agricultural workers and the general public. It is also well-known that the general public would like less chemical residue on fruits and vegetables. A particular consequence of this situation is that there is an increasing need to have more efficient methods of protection of plants such as fruits and vegetables.

The control of phytopathogenic fungi is of great economic importance since fungal growth on plants or on parts of plants inhibits production of foliage, fruit or seed, and the overall quality of a cultivated crop. Because of the vast economic ramifications of fungal propagation in agricultural and horticultural cultivations, a broad spectrum of fungicidal and fungistatic products have been developed for general and specific applications.

Inorganic substances were the first to be used in large-scale crop protection aimed against pathogenic fungi. Notable among these are elemental sulfur applied in powder form, and copper sulfate applied in caustic calcium aqueous mixture (Bordeaux mixture). More complex, synthetic, organic compounds and combinations of organic compounds with metals were developed over the past century with concomitant rise in specific efficacy per unit weight of the active matter. However, such compounds are often environmentally non-recyclable or some of their derivatives are found even toxic to wild life in the environment. Additionally, pathogens often develop resistance to such synthetic pesticides, a fact that promotes a continuous endeavor for developing new crop protecting agents.

In spite of the development of organic chemistry of pesticides, the use of simple structured anti pathogenic compounds has not declined, and constantly new ideas and products of this trend are being unveiled. Fungicide compositions based on copper, zinc or manganese are known to be effective against a broad range of plant pathogenic fungi and bacteria. These include copper hydroxide (Kocide), copper sulfates (Bordeaux mixture), copper oxychlorides and copper oxide. The estimated use of copper hydroxide in the U.S.A. in 1995, for example, was approximately 5 million kg. The reasons for using simple inorganic compounds for control of plant disease are twofold: first, most of the pesticides in this category are environmentally recyclable, and second, the pests do not tend to develop immunity against them. These compounds act upon contact and are applied mainly by foliar spray. The use of these traditional inorganic fungicides for soil treatment is limited due to the absorption of the metal ions to soil particles.

Chelating agents have been used in agriculture for decades as fertilizers of microelements essential for plant growth, i.e. iron, zinc, manganese, copper, etc. The chelating molecule improves the mobility of microelements in the soil, thus enabling the delivery of microelements to the root zone. In addition, the chelating molecule protects the availability of microelements for intake by plant roots.

The combination of metal ions and chelating agents (chelated metals) may be used as effective fungicides for plant disease control as claimed in the Israeli patent IL 97676. However, chelated metals fungicides are phytotoxic at optimal fungicdal dose and therefore not commercially practical.

Phosphorous acid ($H_3PO_3$) or phosphorous acid salts (phosphites or phosphonates) are known to be active against Oomycetes fungi. The mode of action of phosphite as an antifungal agent, involves both direct fungal inhibition as well as induced resistance. The use of compositions containing phosphites for plant disease control was disclosed in U.S. Pat. No. 5,674,536. Said patent discloses fungicide compositions whereby the active substances are a phosphite salt, lecithin, and at least one of the two compounds selected from sodium metasilicate and soda waterglass. U.S Pat. No. 4,075,324 discloses the use of phosphorous acid or the salts thereof as effective fungicides for controlling fungus disease in plants.

The disadvantages of the above described phosphite salt-based compositions and methods relate to their limited efficiency in reducing disease severity relative to alternative synthetic organic fungicides. Moreover, the above described compositions are in a form of a spray and can not be applied directly to the soil since phosphite salt-based compounds tend to be absorbed by soil particles, thereby decreasing their uptake by plant roots.

Thus, it will be highly advantageous to have a safe, environmental recycable and user friendly composition and a method for controlling plant pathogens, that will be efficient and cost effective and will treat and protect plants against foliage and soil-borne pathogens.

SUMMARY OF THE INVENTION

The invention provides a composition for controlling growth of pathological organisms on a plant, said composition comprises an effective amount of one or more of metal ion(s); one or more of chelating agent(s); and phosphorous acid, and/or salt or hydrate thereof, said composition is in an agriculturally compatible carrier or vehicle.

In preferred embodiment, the composition further comprises an acidifying agent so as to form a low pH solution, Lower pH increases the solubility and uptake of metal ion into the roots of plants.

The chelating agents provide a protective coating over metal ions and prevent the absorption of metal ions in soil particles, and increase both the metal's solubility in water and its mobility in wet soil.

The invention further provides a method for controlling growth of pathological organisms on a plant, said method comprising contacting said plant or the soil which surround the plant with an effective amount of a composition comprises one or more of metal ion(s); one or more of chelating agent(s); a phosphorous acid and/or a salt or hydrate thereof, said composition is in an agriculturally compatible carrier, whereby growth of said pathological organisms on said plant is controlled.

The components of the composition possess unexpectedly synergistic interaction of controlling growth of pathological organisms on a plant. Thus, the surprising synergistic activity of the components of the composition of the invention provides an environmentally recyclable solution, which is applicable as both a protective and a curative disease control treatment. The presence of the three different components in the composition that possess synergistic activity prevents the development of resistance by pathogens, provides additional nutritive plant-growth benefits, decreases the cytotoxicity of fungicides to human and mammals and enables a user-friendly method of administration—applicable via the irrigation system.

BRIEF DESCRIPTION OF THE DRAWINGS

The present invention will be understood and appreciated more fully from the following detailed description taken in conjunction with the appended drawings in which.

The term "the soil which surround the plant" refers to the soil which the plant is growing on within the radius of about 2 meters.

The term "metal ion" refers to metal ions which are for example the ions of the elements of the second main group, in particular copper, zinc and magnesium, or the third and fourth main group, in particular aluminum, tin and lead, and of the first to eighth sub-group, in particular chromium, manganese, iron, cobalt, nickel, copper, zinc and others. Especially preferred are the metal ions of the elements of the sub-groups of the fourth period. The metals can exist in the various valences which they can assume.

The term "chelating agent" refers herein above and in the claims section to synthetic or natural molecules that bound to metal ions. Chelating agents are used for keeping divalent and polyvalent metal ions in solutions. The chelating agent can be for example EDTA, EDDHA, HEDTA, DTPA, citrate, saccharate, gluconate, glucoheptonate or glycine.

The term "phosphorous acid or salts and hydrates thereof" refers for example to $K_2HPO_3$, $KH_2PO_3$, $Na_2HPO_3$, $NaH_2PO_3$ or $H_3PO_3$.

The term "$ED_{90}$" refers in the Specifications and in the Examples sections to the concentration required to cause 90% inhibition of the disease severity in treated leaf discs or in whole plants in comparison to the control discs or plants.

DETAILED DESCRIPTION OF THE PRESENT INVENTION

The present invention provides compositions and methods for controlling plant pathogens. The invention is based on the surprising synergistic interaction between a metal ion, a chelating agent and a phosphorous acid and/or salts and hydrates thereof in controlling plant pathogens. The synergistic interaction enables the use of lower concentrations of each of the components, which is economically preferable.

In a preferred embodiment, an acidifying agent is added to the complex. The addition of the acidifying agent results in a low pH of the solution The low pH contributes to the solubility of ionic microelements such as for example, without limitation copper, zinc, and manganese. Moreover, the availability of ionic microelements to plant roots is increased in low pH. Therefore, the acidifying agent in the composition improves solubility, mobility in soil and availability of fungicidal and bacteriocidal ionic metals such as copper and zinc to the plant.

The above composition enables a soluble complex, wherein none of the ingredients precipitate so as to enhance the absorption of the liquid mixture in the soil or into the plant, and thus is in a form available to the plant.

In a preferred embodiment, the present invention relates to method of treating plants against diseases that are caused by plant pathogens. The plant pathogens are microorganisms such as a fungus or a bacterium.

In another embodiment, the composition is characterized in that the phosphorous acid and/or salt or hydrate thereof is present in an amount from about 10% to about 70% by weight of wet composition.

In another embodiment, the composition is characterized in that the metal ion is present in an amount from about 1% to about 10% by weight of wet composition.

In another embodiment, the composition is characterized in that the chelating agent is present in an amount from about 1% to about 10% by weight of wet composition.

In another embodiment, the composition is characterized in that the acidifying acid is present in an amount from about 1% to about 10% by weight of wet composition.

In a preferred embodiment, the ratio (w/w) of Cu: Zn in the composition is 1:2 respectively. The ratio (w/w) of phosphorous acid and/or salt or hydrate thereof to the metal ion and the chelating agent may range between 5:1 to 1:5, respectively.

The total amount of the composition applied for soil application may range between 0.1 to 10 kg of active ingredient per 1000 sq meter. The dose of the composition applied for foliage spray application may range between 0.1% to 2% and the total amount may range between 10 to 100 L per 1000 sq meter. It should be noted that practical application rates are varying according to plant, pathogen and matrix situations.

The composition comprises in addition a suitable carrier. Said carrier may be a natural or synthetic, organic or inorganic material with which the active compounds are combined to facilitate their application into the plant. This vehicle is thus generally inert and it must be acceptable in agriculture. The vehicle can be solid (e.g., clays, natural or synthetic silicates, silica, resins, waxes, or solid fertilizers) or liquid (e.g., water, alcohols, ketones, petroleum fractions, aromatic or paraffinic hydrocarbons, chlorinated hydrocarbons, or liquefied gases).

This composition can also contain any kind of other compatible ingredients such as, for example, protective colloids, adhesives, thickening agents, thixotropic agents, penetrating agents, stabilizing agents, sequestering agents, fertilizers, anti-freeze agents, repellents, color additives, corrosion inhibitors, water-repelling agents, siccatives, UV-stabilizers, pigments, dyes or polymers.

The composition of the present invention may be in a form of solid, powder for dusting or dispersion (with an active compounds content which can range up to 100%), wettable powders and dispersible or soluble granules.

Wettable powders (or powders to be sprayed), as well as dispersible granules, generally contain from about 20 to about 95% of active materials and, in addition to the solid vehicle, from 0 to about 5% of a wetting agent, from about 3 to about 10% of a dispersing agent and, when necessary, from 0 to about 10% of one or more stabilizing agents and/or other additives, such as pigments, dyes, penetrating agents, adhesives, or anticlumping agents. It is well understood that some of these compositions, such as wettable powders or dispersible granules, are intended to constitute liquid compositions at the time of application.

The composition may be in the form of liquid composition, in particular water-soluble concentrates, suspension concentrates or pastes.

The soluble concentrates most often comprise from about 10 to about 80% of active material. The solutions ready for application contain from about 0.01 to about 20% of active material. As mentioned hereinabove, aqueous dispersions, for example, the compositions obtained by diluting a wettable powder according to the invention with water, is within the general scope of the present invention.

The suspension concentrate, also applicable by spraying, is a stable fluid product, which does not thicken or form a sediment after storage, and it generally contains from about 10 to about 75% of active materials, from about 0.5 to about 15% of surface-active agents, from about 0.1 to about 10% of thixotropic agents and from 0 to about 10% of suitable additives, such as pigments, dyes, antifoaming agents, corrosion inhibitors, stabilizing agents, penetrating agents and adhesives and, as vehicle, water or an organic liquid in which the active materials are insoluble or nearly insoluble. Certain organic solid materials or inorganic salts can be dissolved in the vehicle to aid in preventing sedimentation.

Thus, to obtain powders to be sprayed or wettable powders, the active materials are intimately mixed, in suitable mixers, with the additional substances, and the mixture is milled with mills or other grinders. Powders to be sprayed are thereby obtained with advantageous wettability and suspensibility; they can be suspended in water at any desired concentration and these suspensions can be used very advantageously.

Pastes or suspension concentrates can be produced in place of wettable powders. The conditions and modes of production and use of these pastes are similar to those of wettable powders or powders to be sprayed, part of the milling operation necessary simply being carried out in a liquid medium.

The synergistic interaction between the components of the composition of the present invention enhances the activity against a broad range of phytopathogenic fungi and bacteria and particularly the activity against Oomycetes fungi which include species of the genera Pythium, Phytophthora, Peronospora, Pseudoperonospora, Bremia and Albugo.

The synergistic interaction between the components of the composition according to the present invention possess advantageous curative, preventive and systemic fungicidal activity to protect plants, in particular culture plants. The present composition can be used to protect plants or parts of plants, e.g. fruits, blossoms, flowers, foliage, stems, roots, tubers of plants or culture plants infected, harmed or destroyed by microorganisms, whereby later-growing parts of plants are protected against such microorganisms.

The present invention encompasses a composition and method for controlling plant diseases caused by pathogenic microorganisms, wherein a plant or the soil which surround the plant is contacted with an effective amount of a composition comprising (a) zinc and copper metal ions,
(b) one or more chelating agent selected from the group consisting of citric acid, citrates, and mixtures thereof, and
(c) phosphorous acid, and/or salt or hydrate thereof, wherein (i) said composition is in an agriculturally compatible carrier or vehicle; (ii) said composition contains (a), (b) and (c) in a proportion so that, when wet, (a) is present in an amount that is greater than 0% by weight and no greater than about 10% by weight, (b) is present in an amount that is greater than 0% by weight and no greater than about 10% by weight, and (c) is present in an amount that is greater than 0% by weight and no greater than about 70% by weight; and (iii) said composition provides a synergistic control of said plant diseases that is greater than the additive sum of control provided by (c) and control provided by combination of (a) and (b);

thereby controlling said plant diseases caused by pathogenic microorganisms.

The composition according to the present invention show systemic activity. The composition can further be used in seed disinfection (fruits, tubers, cereal grains) and to treat plant cuttings as well as to combat phytopathogenous fungi occurring in the soil. The composition of the present invention is particularly attractive due to its good plant tolerance and lack of environmental problems (low application rates).

As examples of the wide variety of culture plants in which the combinations of active ingredients according to the present invention can be used, there may be named for example cereals, e.g. wheat, barley, rye, oats, rice, sorghum and the like; beets, e.g. sugar beet and fodder beet; pome and stone fruits and berries, e.g. apples, pears, plums, peaches, almonds, cherries, strawberries, raspberries and blackberries; leguminous plants, e.g. beans, lentils, peas, soy beans; oleaginous plants, e.g. rape, mustard, poppy, olive, sunflower, coconut, castor-oil plant, cocoa, ground-nuts; cucurbitaceae, e.g. pumpkins, gherkins, melons, cucumbers, squashes; fibrous plants, e.g. cotton, flax, hemp, jute; citrus fruits, e.g. orange, lemon, grapefruit, mandarin; vegetables, e.g. spinach, lettuce, asparagus, brassicaceae such as cabbages and turnips, carrots, onions, tomatoes, potatoes, hot and sweet peppers; laurel-like plants, e.g. avocado, cinnamon, camphor tree;: or plants such as maize, tobacco, nuts, coffee, sugar-cane, tea, vines, hops, bananas, rubber plants, as well as ornamental plants, e.g. flowers, shrubs, deciduous trees and evergreen trees such as conifers. This enumeration of culture plants is given with the purpose of illustrating the invention and not to delimiting it thereto.

EXAMPLES

The first set of experiments illustrated in Examples 1–6 was assessed using *Phytophthora infestans* (*P. infestans*) and *Pythiun ultimum* (*P. ultimum*).

Materials and Methods:

Several isolates of *P. infestans* were used for inoculation, either sensitive or resistant to metalaxyl One isolate of *P. ultimum*, isolated from cucumber was used. Sporangia of *P. infestans* were collected from infected potato tuber slices, whereas inoculunm of *P. ultimum* was prepared by homogenizing Potato Dextrose Agar (PDA) cultures with the fungus.

Sporangia of *P. infetans* were applied onto leaf discs of potato or tomato or to whole plants to evaluate the control of late blight disease, caused by *P. infestans*, or to the soil-mix in pots to evaluate the control efficacy of damping-off disease, caused by *P. ultimum*, in cucumber. The tests with *P. infestans* were conducted in growth chamber at 18–21° C., whereas those with *P. ultimum* were conducted in the greenhouse at 20–33° C., Experimental Results Example 1

Fungicidal Activity of Metal Ion and Chelating Agent in vitro Tested by the Leaf Disc Bioassay The concentration of the metal ion and the chelating agent (referred herein as "AG composition") is as follows (g/L): ZnO, 66; Citric Acid, 254; $CuSO_4 \cdot 5H_2O$, 104.

Figure 1:
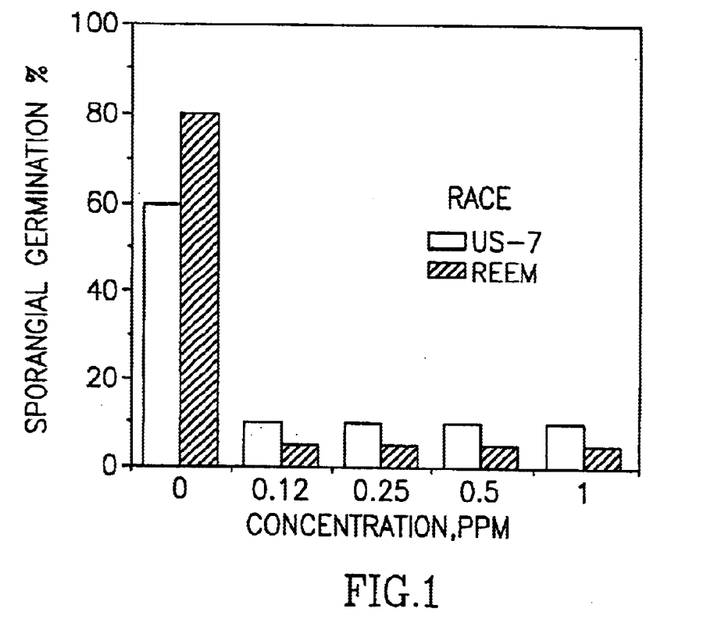
FIG. 1 is a presentation of the fungicidal activity against sporangia of *Phytophthora Infestans* in vitro.

AG composition exhibited strong fungicidal activity in vitro against sporangia of *P. infestans* in vitro, which is demonstrated in FIG. 1. When AG composition was diluted to 0.06% of active ingredient, the sporangial germination was reduced by 82 and 93%, in two *P. infestans* isolates, US-7 and Reem, respectively.

Figure 2:
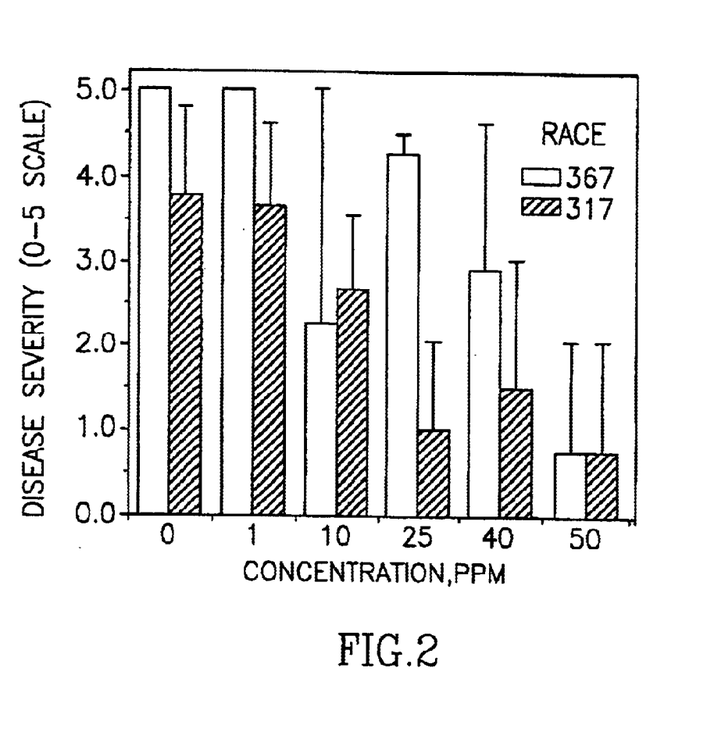
FIG. 2 is a presentation of the inhibition of late blight in tomato leaf discs by the composition of the invention 50 ppm.
Figure 3:
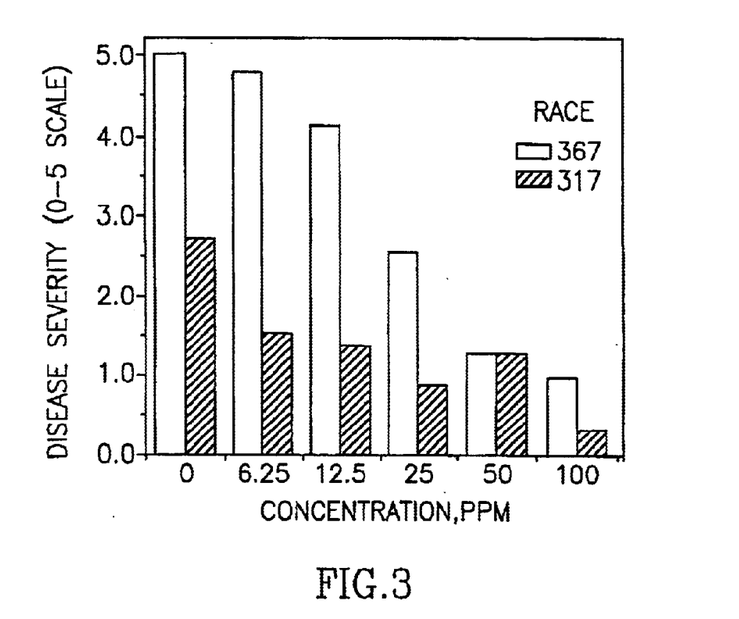
FIG. 3 is a presentation of the inhibition of late blight in tomato leaf discs by the composition of the invention 100 ppm.
Figure 4:
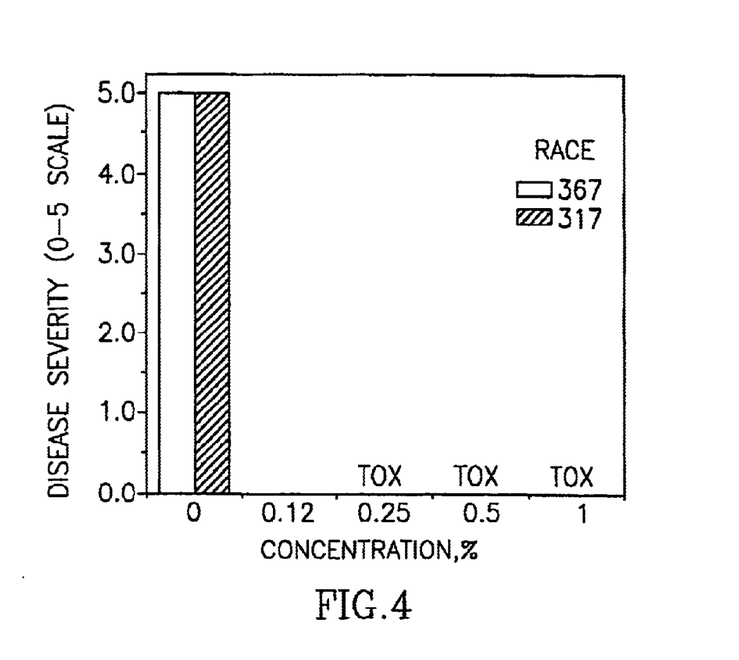
FIG. 4 is a presentation of the total disease inhibition by the composition of the invention.
Figure 5:
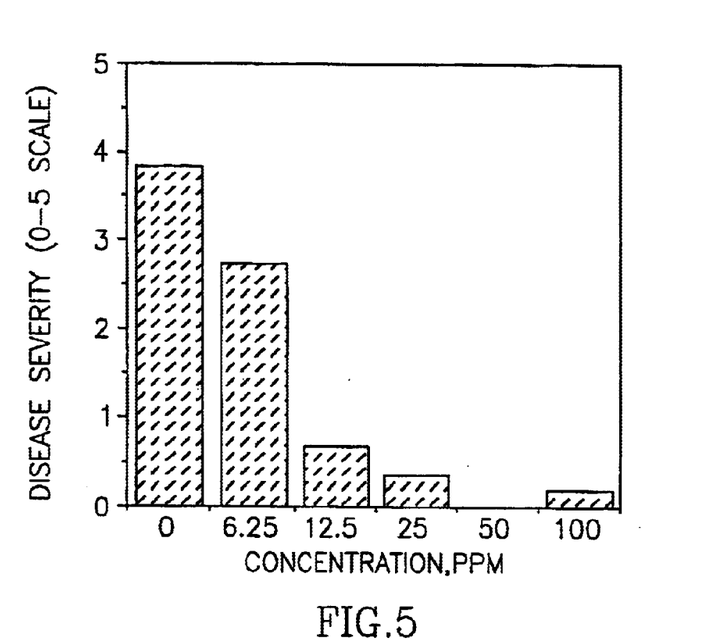
FIG. 5 is a presentation of the abolishment of the downy mildew development in melon leaf discs inoculated with a metalaxyl-resistant isolate of *Pseudoperonospora cubensis*.

The severity of late blight disease in tomato leaf discs was inhibited by 86 and 79% with 50 ppm of AG composition in *P. infestans* isolates 367 and 317, respectively (FIG. 2), and by 81 and 87% with 100 ppm (FIG. 3). With isolated Mivtahim a total inhibition was obtained with 62 ppm of the composition (data not shown). FIG. 4 demonstrates a total inhibition of the disease at 0.12% of active ingredient of AG composition. A slight phytotoxicity appeared when AG composition was used at 0.25% of active ingredient. 50–100 ppm of AG composition has almost abolished the development of downy mildew in melon leaf discs inoculated with a metalaxyl-resistant isolate of *Pseudoperonospora cubensis* (data not shown).

Example 2

The Synergistic Effect of AG Composition Applied with Phosphorous Acid (PA) or with Photassium Phosphite (PP) in Controlling Fungus in vitro The effect of AG composition in combination with Phosphorous Acid (PA) or Potassium Phosphite (PP) in controlling late blight in tomato leaf discs was assessed as follows: a dose response curve was conducted when AG composition, PA and PP were applied separately, and when AG composition was applied in combination with PA or PP. $ED_{90}$ value (which is the concentration required to cause 90% inhibition of the disease in treated leaf discs relative to control-inoculated discs) was used to obtain the synergy factor (SF) according to Wadely. A SF value higher than 1 indicates a synergistic interaction. Table 1 below clearly shows that in both AG composition+PA and AG composition+PP combinations, there is a synergistic effect at either 1:1 or 2:1 ratios. Thus, a significant synergistic effect of AG composition and PA or PP is evident in leaf disc bioassay. This example indicates that both $H_3PO_3$ and $KH_2PO_3$ administered together with AG composition, have a lower $ED_{90}$ than each of the components alone.

TABLE 1

Synergistic interaction between AG composition and Phosphorous Acid (PA) or Potassium Phosphite (PP) in controlling P. infestans in tomato leaf discs

| Compound or mixture | $ED_{90}$ | synergy Factor (SF) |
|---|---|---|
| AG* | 101 | |
| $H_3PO_3$ | 45 | |
| $K_3PO_3$** | 130 | |
| AG + $H_3PO_3$ (1:1) | 31 | 2.0 |
| AG + $H_3PO_3$ (2:1) | 40 | 1.8 |
| AG + $K_3PO_3$ (1:1) | 102 | 1.1 |
| AG + $K_3PO_3$ (2:1) | 41 | 2.7 |

*49% solids
**16% $KH_2PO_3$

Example 3

The Synergistic Effect of AG Composition Applied with Photassium Phosphite (PP) in Controlling Fungus in Whole Plant Assay The effect of AG composition in combination with Phosphorous Acid (PA) or Potassium Phosphite (PP) in controlling late blight caused by P. infestans in intact potted tomato and potato was assessed as in Example 2. Table 2 below clearly shows that AG composition and PP interact synergistically at 1:3 ratio in tomato and at 1:1 ratio in potato.

TABLE 2 synergistic interaction between AG composition and PP in controlling *P. Infestans* in tomato and potato

| Compound or mixture | $ED_{90}$ | Synergy Factor (SF) |
|---|---|---|
| TOMATO | | |
| AG | 0.71 | — |
| $K_3PO_3$ | 1.10 | — |
| AG + $K_3PO_3$ (1:1) | 0.98 | 0.9 |
| AG + $K_3PO_3$ (1:3) | 0.66 | 1.4 |
| AG + $K_3PO_3$ (3:1) | 0.91 | 0.9 |
| POTATO | | |
| AG | 0.54 | |
| $K_3PO_3$ | 0.52 | |
| AG + $K_3PO_3$ (1:1) | 0.35 | 1.5 |
| AG + $K_3PO_3$ (1:3) | 0.68 | 0.8 |
| AG + $K_3PO_3$ (3:1) | 0.59 | 0.9 |

Example 4

The Synergistic Effect of AG Composition Applied with Photassium Phosphite (PP) in Controlling Fungus when Administered to the Plant by Spraying The effect of AG composition in combination with Potassium Phosphite (PP) in controlling fungus when administered to the plant by spraying was assessed as in Example 2. Table 3 below clearly shows that AG composition and PP interact synergistically at 1;3 ratio in tomato and at 1:1 and 1:3 ratios in potato.

TABLE 3

Control of *P. infestans* in potato and tomato with AG composition + K₃PO₃ 40% (Australia)

| | Tomato | | | Potato | |
|---|---|---|---|---|---|
| Treatment | Inhibition (% of control) | ED₉₀ | Synergy Factor (SF) | Inhibition (% of control) | ED₉₀ | Synergy Factor (SF) |

| Treatment | Inhibition (% of control) | ED$_{90}$ | Synergy Factor (SF) | Inhibition (% of control) | ED$_{90}$ | Synergy Factor (SF) |
|---|---|---|---|---|---|---|
| AG (% active ingredient) | | | | | | |
| 0.12 | 0 | | | 75 | | |
| 0.25 | 13 | | | 78 | | |
| 0.5 | 25 | | | 78 | | |
| 1.0 | 44 | 1.73 | — | 85 | 0.88 | — |
| | Toxic | | | Toxic | | |
| K$_3$PO$_3$ (% active Ingredient) | | | | | | |
| 0.12 | 50 | | | 83 | | |
| 0.25 | 63 | | | 63 | | |
| 0.5 | 86 | | | 85 | | |
| 1.0 | 98 | 0.55 | — | 90 | 0.70 | — |
| AG + K$_3$PO$_3$ (1:1 ratio) | | | | | | |
| 0.12 | 38 | | | 70 | | |
| 0.25 | 56 | | | 78 | | |
| 0.5 | 76 | | | 80 | | |
| 1.0 | 94 | 0.73 | 1.1 | 98 | 0.55 | 1.4 |
| AG + K$_3$PO$_3$ (1:3 ratio) | | | | | | |
| 0.12 | 81 | | | 78 | | |
| 0.25 | 85 | | | 78 | | |
| 0.5 | 86 | | | 93 | | |
| 1.00 | 99 | 0.43 | 1.5 | 100 | 0.35 | 2.1 |
| AG + K$_3$PO$_3$ (3:1 ratio) | | | | | | |
| 0.12 | 38 | | | 70 | | |
| 0.25 | 38 | | | 70 | | |
| 0.5 | 38 | | | 85 | | |
| 1.00 | 69 | 1.47 | 0.8 | 63 | 0.94 | 0.9 |

TABLE 4

Control of *P. infestans* in potato and tomato with AG composition + H₃PO₃

| | Tomato | | | Potato | | |
|---|---|---|---|---|---|---|
| Treatment | Inhibition (% of control) | ED$_{90}$ | Synergy Factor (SF) | Inhibition (% of control) | ED$_{90}$ | Synergy Factor (SF) |
| AG (% active ingredient) | | | | | | |
| 0.12 | 25 | | | 62 | | |
| 0.25 | 50 | | | 75 | | |
| 0.5 | 50 | | | 82 | | |
| 1.0 | 63 | 1.49 | — | 97 | 0.57 | — |
| | Toxic | | | | | |
| H$_3$PO$_3$ (% active Ingredient) | | | | | | |
| 0.01 | 13 | | | 25 | | |
| 0.02 | 13 | | | 37 | | |
| 0.05 | 19 | | | 49 | | |
| 0.1 | 31 | 2.52 | — | 62 | 1.50 | — |
| AG + H$_3$PO$_3$ (1:1 ratio) | | | | | | |
| 0.12 | 83 | | | — | | |
| 0.25 | 83 | | | 85 | | |
| 0.5 | 100 | | | 85 | | |
| | Toxic | | | | | |
| 1.0 | 94 | 0.32 | 5.8 | 100 | 0.45 | 1.8 |
| | Toxic | | | | | |
| AG + H$_3$PO$_3$ (5:1 ratio) | | | | | | |
| 0.12 | 58 | | | 62 | | |
| 0.25 | 75 | | | 68 | | |
| 0.5 | 81 | | | 75 | | |
| | Toxic | | | | | |
| 1.00 | 94 | 0.79 | 2.0 | 77 | 1.09 | 0.6 |
| | Toxic | | | | | |
| AG + H$_3$PO$_3$ (10:1 ratio) | | | | | | |
| 0.12 | 58 | | | 62 | | |
| 0.25 | 75 | | | 82 | | |
| 0.5 | 81 | | | 82 | | |
| | toxic | | | | | |
| 1.00 | 94 | 0.66 | 2.4 | 97 | 0.56 | 1.2 |
| | Toxic | | | Toxic | | |

Example 5

The Synergistic Effect of AG Composition Applied with Phosphorous acid (PA) in Controlling Fungus when Administered to the Plant by Spraying The effect of AG composition in combination with phosphorous acid (PA) in controlling fungus when administered to the plant by spraying was assessed as in Example 2. Table 4 below clearly shows that AG composition and PA interact synergistically at 1:1, 5:1 and 10:1 ratios in tomato and at 1:1 and at 1:1 ratio in potato.

Example 6

The Synergistic Effect of AG Composition Applied with Phosphorous Acid (PA) or with Photassium Phosphite (PP) in Controlling *P. ultimum*

Another series of experiments were conducted with *P. ultimum*, The fungus was mixed with the substrate (peat+perlite, 1:1 ratio, v/v), drenched with 10 ml of the compounds or their mixtures (1:1 ratio only) and cucumber seeds were planted. Damping-off disease incidence was monitored after a week. The results indicated that 0.5% of AG composition alone was required for a total control of the disease, whereas a mixture containing 0.06%+0.06% of AG+PA or 0.12%+0.12%% of AG+PP was sufficient to obtain the same level of pathogen control (data not shown).

Thus, all the examples above indicate that fungal pathogens of the Oomycetes are sensitive to each of the AG composition, phosphorous Acid and Potassium Phosphite compounds. However, Oomycetes are more sensitive to the combination of AG composition with Phosphorous Acid or with Potassium Phosphite. This sensitivity was expressed by the ability of these compounds to control late blight disease in tomato leaf discs, fungus disease in tomato and potato plants after foliar application and damping-off disease in cucumber after soil drench.

Another set of experiments illustrated in Examples 7–10 were conducted with the composition refers herein bellow as "AG3" which comprises the following ingredients (g/L): $H_3PO_3$ 101.4; KOH 145.5; Citric Acid 46.8; $ZnSO_4*7H_2O$ 9.2; $CuSO_4*5H_2O$ 4.0 (pH=6.8, 15% active ingredient)).

Example 7

Figure 6:
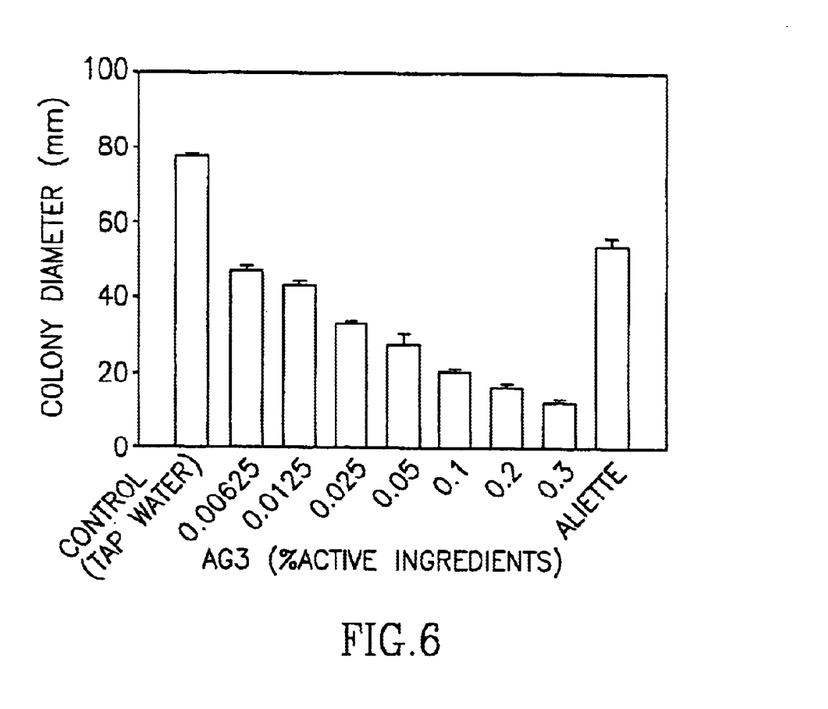
FIG. 6 is a presentation of the effect of different concentrations of AG3 on colony growth of *Pythium aphanidermatum*.

Inhibition of Pythium aphanidermatum Mycelial Growth in vitro by AG3 Composition The pathogenic fungus Pythium aphanidermatum (P. aphanidermatum) was cultured on diluted V-8 juice agar supplemented with 1.5% cholesterol. The culture medium was supplimented with AG3 composition at different concentrations ranging from zero to 0.3% of active ingredients. Mycelial disks of P. aphanidermatum were placed at the edge of 9 cm plates, incubated at 25° C. in the dark for 24 hr and the orthogonal colony diameters were then measured. The effect of AG3 composition was compared with the commercial fungicide, Fosetyl-Al (Aliette 80% WP) at the recommended concentration of 0.07% of active ingredient. The results (FIG. 6) show that AG3 composition diluted to 0.006% or 0.01% of active ingredient inhibited P. aphanidermatum radial growth in vitro by 50%, which is the same level of inhibition caused by the commercial fungicide Fosetyl-Al (Aliette) at the recommended dosage of 0.07% of active ingredient.

Example 8

Suppression of Pythium Damping-Off Disease in Cucumber Seedlings by AG3 Composition Commercial potting mix (ProMix) was mixed with sand (1:5) and moistened with tap water to a standard 3 L/kg ProMix-sand mix. P. aphanidermatum inoculum for artificial infestation was produced in autoclaved V-8 juice-cholesterol broth and consisted of oospores at $2\times10^3$ cfu/ml applied as an aqueous drench. AG3 composition was diluted with tap water at different concentrations and was added as a drench prior to planting. The efficacy of AG3 composition was compared to the commercial fungicide Fosetyl-Al (Aliette) applied similarly at a recommended concentration of 0.07% of active ingredient. ProMix flats (30×15×8 cm) were seeded with cucumber seeds (cv. Straight Eight) and incubated in a growth room. After 10 days the number of seedlings surviving damping-off was recorded and a percentage survival (emergence) was calculated. Three replicates of each treatment were arranged in a completely randomized design and the experiment was repeated at least once.

Figure 7:
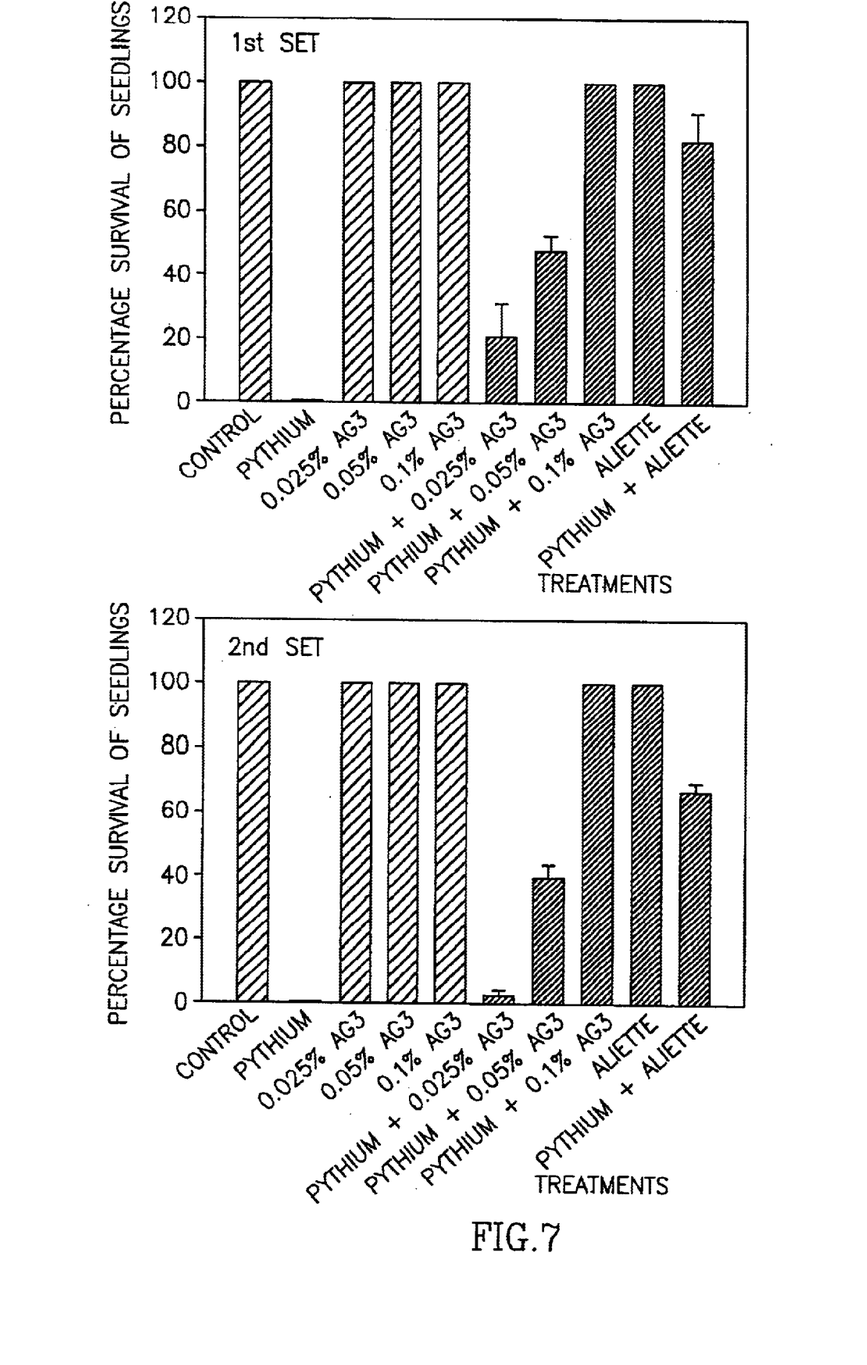
FIG. 7 is a presentation of the percent survival of cucumber seedlings inoculated with *Pythium aphaniderrmatum* at different levels of AG3.

The results (FIG. 7) Show that in Pythium-inoculated flats, no plant survived in fungicide untreated flats. On the other hand, all plants (100%) survived in Pythium-inoculated flats that were drenched with AG3 composition at 0.1% of active ingredient. Only 70–80% of plants survived in Pythium-inoculated flats drenched with the commercial fungicide Aliette applied at a recommended concentration of 0.07% of active ingredient.

Example 9

Suppression of Rhizoctonia Damping-Off Disease in Tomato Seedlings by AG3 Composition Mycellial biomass of the pathogenic fungus Rhizoctonia solani was filtered and the macerated mycelial ($2\times10^4$ cfu/mL) was added to ProMix in flats. AG3 composition was applied before seeding as an aqueous drench at three dosages, 0.025%, 0.05% and 0.1% of active ingredient Tomato seedlings (cv Bonny Best) showing damping-off symptoms Were counted after 21 days of incubation in the greenhouse at 25° C. and percentage damping-off was calculated based on the number of seedlings having emerged after 7 days.

The incidence of damping-off in tomato seedlings by R. solani was reduced significantly by pre-seeding drench applications of aqueous AG3 composition to the artificially infested ProMix. The level of disease suppression achieved with AG3 composition 0.1% active ingredient was 92%, compared with untreated control (not shown).

Example 10

Suppression of Phytophthora Root Disease in Citrus Seedlings

Citrus seedlings (cv Walkmarina) were germinated in flats. AG3 composition was applied to one month old seedlings as an aqueous drench at three dosages, 0.1%, 0.5% and 1% of active ingredient. Treatment with Water only (0%) was used as control. After 24 hours all seedlings were taken out, washed and roots were dipped into the inoculum suspension for eight hours. Inoculum of the pathogenic fungus Phytophthora citrophthora (P. citrophthora) was prepared by washing zoospores of a 5-day old culture with sterile cold water. Inoculated seedlings were planted in 6" pots filled with water-saturated sand. AG3 composition at the three different dosages, or water-only control, were applied after planting as aqueous drench to the pots. Six weeks after inoculation, seedlings were taken out and the number of healthy rootlets and the number of leaves were recorded.

Table 5 shows that citrus seedling infected with P. citrophthora and treated with AG3 composition 0.1% of active ingredient developed 11.3 fold more roots and 9.8 fold more leaves than infected and fungicide untreated seedlings.

TABLE 5

Control of Phytophthora citrophthora root disease in citrus seedlings with AG3 composition.

| Treatment | Average number of roots | Average number of leaves |
|---|---|---|
| Control non-infected | 6.9 | 4.3 |
| Control infected | 1.2 | 0.9 |
| AG3 0.1% | 13.5 | 8.8 |
| AG3 0.5% | 10.2 | 3.9 |
| AG3 1% | 12.3 | 8.2 |

What is claimed is:

1. A composition for controlling plant diseases caused by pathogenic microorganisms comprising an effective amount of:
   (a) zinc and copper metal ions;
   (b) one or more chelating agent selected from the group consisting of citric acid, citrates, and mixtures thereof; and
   (c) phosphorous acid, and/or salt or hydrate thereof;
   wherein (i) said composition is in an agriculturally compatible carrier or vehicle;
   (ii) said composition contains (a), (b) and (c) in a proportion so that, when wet, (a) is present in an amount that is greater than 0% by weight and no greater than about 10% by weight, (b) is present in an amount that is greater than 0% by weight and no greater than about 10% by weight, and (c) is present in an amount that is greater than 0% by weight and no greater than about 70% by weight; and (iii) said composition provides a synergistic control of said plant diseases that is greater than the additive sum of control provided by (c) and control provided by combination of (a) and (b).

2. The composition of claim 1, further comprising an effective amount of an acidifying agent.

3. The composition of claim 1, further comprising one or more of protective colloids, adhesives, thickening agents, penetrating agents, stabilizing agents, sequestering agents, fertilizers, anti-freeze agents, repellents, color additives, corrosion inhibitors, water-repelling agents, siccatives, UV-stabilizers, pigments, dyes and polymers.

4. The composition of claim 1, wherein said phosphorous acid salt is $K_2HPO_3$, $KH_2PO_3$, $Na_2HPO_3$ or $NaH_2PO_3$.

5. The composition of claim 2, wherein said acidifying agent is citric acid, fulvic acid, lignosulfonate, or sulfuric acid.

6. The composition of claim 1, wherein said phosphorous acid, the salt or hydrate thereof is present in an amount from about 10% to about 70% by weight of a wet composition.

7. The composition of claim 1, wherein said zinc and copper metal ions are present in an amount from about 1% to about 10% by weight of a wet composition.

8. The composition of claim 1, wherein said chelating agent is present in an amount from about 1% to about 10% by weight of a wet composition.

9. The composition of claim 1 wherein said composition is in a form of a solid, a powder, liquid, a paste or a spray.

10. The composition of claim 1, wherein said Pathogenic microorganisms are fungi or bacteria.

11. The composition of claim 10, wherein said fungi are selected from the group consisting of Phytophthora, Peronospora, Pseudoperonospora, Pythium, Rhizoctonia, Bremia and Albugo.

12. The composition of claim 10, wherein said bacteria are selected from the group consisting of Pseudomonas, Xanthomonas and Erwinia.

13. The composition of claim 1, wherein the ratio between a first component comprising said zinc and copper metal ions and said one or more chelating agent and a second component comprising said phosphorous acid, the salt or hydrate thereof is 1:1 on a weight to weight basis.

14. The composition of claim 1, wherein a ratio between a first component comprising said zinc and copper metal ions and said one or more chelating agent and a second component comprising said phosphorous acid, the salt or hydrate thereof is 1:3 on a weight to weight basis.

15. The composition of claim 1, wherein a ratio between a first component comprising said zinc and copper metal ions and said one or more chelating agent and a second component comprising said phosphorous acid, the salt or hydrate thereof is 3:1 on a weight to weight basis.

16. A method for controlling plant diseases caused by pathogenic microorganisms, said method comprising the step of:

Contacting a plant or the soil which surround the plant with an effective amount of a composition comprising (a) zinc and copper metal ions, (b) one or more chelating agent selected from the group consisting of citric acid, citrates, and mixtures thereof, and (c) phosphorous acid, and/or salt or hydrate thereof;

wherein (i) said composition is in an agriculturally compatible carrier or vehicle;

(ii) said composition contains (a), (b) and (c) in a proportion so that, when wet, (a) is present in an amount that is greater than 0% by weight and no greater than about 10% by weight, (b) is present in an amount that is greater than 0% by weight and no greater than about 10% by weight, and (c) is present in an amount that is greater than 0% by weight and no greater than about 70% by weight; and (iii) said composition provides a synergistic control of said plant diseases that is greater than the additive sum of control provided by (c) and control provided by combination of (a) and (b);

thereby controlling said plant diseases caused by pathogenic microorganisms.

17. The method of claim 16 wherein said composition further comrising an acidifying agent.

18. The method of claim 16, wherein said phosphorous acid salt is $K_2HPO_3$, $KH_2PO_3$, $Na_2HPO_3$ or $NaH_2PO_3$.

19. The method of claim 17, wherein said acidifying agent is citric acid, fulvic acid, lignosulfonate or sulfuric acid.

20. The method of claim 16, wherein said phosphorous acid, the salt or hydrate thereof is present in an amount from about 10% to about 70% by weight of a wet composition.

21. The method of claim 16, wherein said zinc and copper metal ions are present in an amount from about 1% to about 10% by weight of a wet composition.

22. The method of claim 16, wherein said chelating agent is present in an amount from about 1% to about 10% by weight of a wet composition.

23. The method of claim 16, wherein said composition is in a form of a solid, a powder, liquid, a paste or a spray.

24. The method of claim 16, wherein said Pathogenic microorganisms are selected from the group consisting of fungi and bacteria.

25. The method of claim 24, wherein said fungi is selected from the group consisting of Phytophthora, Peronospora, Pseudoperonospora, Pythium, Rhizoctonia, Bremia and Albugo.

26. The method of claim 24, wherein the bacteria is selected from the group consisting of Pseudomonas, Xanthomonas and Erwinia.

* * * * *